(12) United States Patent
Wieselthaler

(10) Patent No.: US 9,144,669 B2
(45) Date of Patent: Sep. 29, 2015

(54) IMPLANTATION PROCEDURE FOR BLOOD PUMPS

(75) Inventor: Georg Wieselthaler, Vienna (AT)

(73) Assignee: HeartWare, Inc., Miami Lakes, FL (US)

( * ) Notice: Subject to any disclaimer, the term of this patent is extended or adjusted under 35 U.S.C. 154(b) by 2046 days.

(21) Appl. No.: 11/280,030

(22) Filed: Nov. 16, 2005

(65) Prior Publication Data
US 2007/0112325 A1    May 17, 2007

(51) Int. Cl.
  *A61M 1/10* (2006.01)
  *A61M 31/00* (2006.01)
  *A61M 1/12* (2006.01)
  *A61B 17/00* (2006.01)

(52) U.S. Cl.
  CPC ............ *A61M 31/002* (2013.01); *A61M 1/10* (2013.01); *A61M 1/1008* (2014.02); *A61M 1/122* (2014.02); *A61B 2017/00252* (2013.01)

(58) Field of Classification Search
  CPC .......... A61M 1/10; A61M 2001/1008; A61M 1/1008; A61M 1/122; A61B 17/11; A61B 2017/00252; A61B 2017/1107; A61B 18/1492; A61B 17/00234; A61B 17/0469; A61B 17/0401; A61B 2017/00243; A61B 2017/00247
  USPC .................. 600/16; 604/9; 623/3.26, 904
  See application file for complete search history.

(56) References Cited

U.S. PATENT DOCUMENTS

2001/0003795 A1 * 6/2001 Suresh et al. ............ 604/96.01
2004/0236170 A1 * 11/2004 Kim .............................. 600/16
2004/0267086 A1 * 12/2004 Anstadt et al. ................. 600/17

OTHER PUBLICATIONS

Hill JD, Avery GJ, Egrie G, Turley K, Reichenback S. Less invasive Thoratec LVAD insertion: A surgical technique. The Heart Surgery Forum 2000; 3(3):218-223.*

* cited by examiner

*Primary Examiner* — Tammie K Heller
(74) *Attorney, Agent, or Firm* — Lerner, David, Littenberg, Krumholz & Mentlik, LLP

(57) ABSTRACT

A surgical procedure including making an incision in the patient's body, inserting at least two sutures close to the junction of the pericardium on the upper right pulmonary vein and making an incision in the pericardium substantially parallel to the ascending portion of the aorta. An incision is made between the sutures on the upper right pulmonary vein, an inflow cannula is inserted into the vein and through the mitral-valve into the left ventricular chamber and the inflow cannula is secured to the upper right pulmonary vein. The procedure includes inserting a blood pump having an outflow graft into the patient's body and cutting the outflow graft to a desired length, attaching a clamp to the aorta and then attaching the outflow graft to the aorta. The clamp is removed and air is flushed or removed from the outflow graft and the blood pump. The blood pump is then connected to the inflow cannula.

44 Claims, 2 Drawing Sheets

IMPLANTATION PROCEDURE FOR BLOOD PUMPS

BACKGROUND

Thousands of heart patients who suffer from severe left ventricular heart failure could benefit from cardiac transplantation. However, because of a shortage of donor hearts, most of these patients face a shortened life span characterized by frequent hospitalizations, severe physical disability, and death from congestive failure or cardiogenic shock.

One medical device developed to aid these heart patients is a heart pump such as a left ventricular assist device ("LVAD") which enables heart failure patients to return to prolonged and productive lives. Most heart pumps or cyclic delivery systems are physically large and complex and make implantation difficult or impossible for some patients. Even when the heart pumps can be implanted, the surgical implant procedure is highly invasive.

Conventional implant procedures use median sternotomy, and in some cases, thoracotomy to insert the heart pumps or LVADs in a patients' body. A median sternotomy is a lengthwise incision through the breastbone (or sternum) that is made when heart surgery or other invasive surgery in the chest cavity is performed. Similarly, a thoracotomy is a surgical procedure for opening the chest wall in order to access the lungs, esophagus, trachea, aorta, heart and diaphragm. Depending on the disease location, thoracotomy may be done on the right or left chest. Pump implants via sternotomy or thoracotomy are highly invasive procedures which are complex, expensive and require relatively long patient recovery time.

Accordingly, there is a need for a less invasive surgical heart pump implant procedure which is simple, less expensive and minimizes patient recovery time. The use of such an implant procedure has become possible due to the development of a specially shaped inflow cannula and a LVAD that has a small displaced volume.

SUMMARY

The present invention is directed to a surgical procedure and, more specifically, to a method for implanting a blood pump in a person's body which is minimally invasive and significantly reduces the costs and patient recovery time associated with such procedures.

In one embodiment, the surgical procedure of the present invention includes installing a single-lung ventilation of the left lung of a patient's body to provide adequate oxygenation to the patient during the surgical procedure. After the ventilator is attached, an incision is made in the patient's body between the fourth and fifth ribs (i.e., the fourth intercostals space) on the right side of the patient's body. It should be appreciated that the incision may be made at any suitable location on the patient's body. The incision may be made by performing a thoracotomy or using any other suitable procedure. In an embodiment, the length of the incision is approximately three inches which is a significant reduction in the size of the opening commonly used to perform such procedures.

After the incision is made, at least two concentric purse-string sutures are inserted to the upper pulmonary vein close to the junction of the pericardium. An incision is then made in the pericardium substantially parallel to the ascending portion of the aorta. A further incision is made between the purse-string sutures on the upper right pulmonary vein to enable an inflow tube such as an inflow cannula to be inserted into the vein. This incision may be a cross-wise incision or any suitable incision. Before this incision is performed, elevated positive airway pressure is applied to the single ventilated left lung, in order to prevent air-suction into the left atrium. In one embodiment, the whole procedure is performed under insufflation of $CO_2$ into the right pleural cavity. The inflow cannula is inserted through the mitral-valve and into the left ventricular chamber of the patient's heart. The inflow cannula has a predetermined size, length and shape. These characteristics can be determined by performing a Computed Tomography (CT) scan prior to performing the surgical procedure or by using any suitable method.

The inflow cannula is secured or connected to the upper right pulmonary vein by tightening the sutures, sewing or stitching the inflow cannula in place or using any suitable method. In one embodiment, the insertion of the inflow cannula is monitored by directing at least one and preferably a plurality of x-rays at the surgical location or using transesophageal echo (TEE) as means of guidance. As described above, the pictures generated by the x-rays are viewed on a display device to assist with the procedure. Any other suitable monitoring device or method may be used to view exact positioning of the inflow tube or inflow cannula associated with the surgical procedure.

A blood pump such as a LVAD described above is inserted into the patient's body and more specifically, is connected to the heart to assist in pumping blood through the body. In one embodiment, the blood pump includes an outflow tube or outflow graft. The outflow graft is cut to a desired length based on the size and shape of the patient's body and the location of the ascending portion of the aorta. A clamp is tangentially attached to the ascending portion of the aorta to allow attachment of the outflow graft to the aorta. Once the tangential clamp is attached and secured to the aorta, the outflow graft of the blood pump is attached to the aorta. In one embodiment, the outflow graft is attached to the aorta by performing a surgical sewing procedure such as an end-to-side anastomosis. After the outflow graft is attached, the clamp is removed from the aorta. The outflow graft and blood pump are then flushed to remove any air that may be in either of these components. The blood pump is connected to the inflow cannula and the incision made in the patient's body is closed such as by sewing or stitching the sides of the opening together to complete the surgical procedure.

In another embodiment, a balloon-tipped catheter can be used within the inflow cannula to prevent the flow of blood during the positioning of the inflow cannula.

In one embodiment, the inflow cannula described above is a substantially rigid tube having a distal end and a proximal end, at least one bend and a curved portion or curvature adjacent to the proximal end. The length, the number and shape of the curves and the location of the curves of the cannula are determined by the size and shape of a patient's body and the location of the heart and the veins attaching to the heart. In one embodiment, the inflow cannula includes a diameter between 6 and 9 mm. It should be appreciated that the inflow cannula may have any suitable size, shape or diameter. The inflow cannula may also be made of titanium, silicone or any other suitable material or combination of materials. In one embodiment, at least one end of the inflow cannula includes a removable balloon-tipped catheter as described above.

In another embodiment, the surgical procedure of the present invention includes installing a single lung ventilation of the left lung of a patient's body and then making an incision in the patient's body between the fourth and fifth ribs as described above. At least two concentric purse-string sutures are inserted close to the junction of the pericardium on the upper right pulmonary vein to define and secure an incision area. The next part of the surgical procedure includes two incisions. One incision is made in the pericardium substantially parallel to an ascending portion of the aorta. The second incision is made between the sutures on the upper right pulmonary vein. In this embodiment, before inserting the blood pump in the patient's body, an end cap is connected to the blood pump and then to an inflow cannula. Pre-connecting the blood pump and inflow cannula in this manner helps to minimize the difficulty and time required to complete the procedure.

Next, the blood pump with an attached outflow graft and inflow cannula are inserted into the patient's body. The inflow cannula is then inserted into the upper right pulmonary vein, through the mitral-valve and into the left ventricular chamber of the heart. The inflow cannula can then be secured to the upper right pulmonary vein as described above. The outflow graft is cut to a desired length. To attach the outflow graft to the aorta, a clamp is placed tangentially to the ascending portion of the aorta. The outflow graft is then attached to the aorta. Afterwards, the clamp is removed from the aorta and the outflow graft and the blood pump are flushed to remove any air in these components. The blood pump is connected to the inflow cannula and the access opening or incision in the patient's body is closed using sutures or other suitable methods to complete the procedure.

The above surgical procedures are generally used to connect or install a blood pump such as a LVAD to the left side of a patient's heart to assist the blood flow on this side of the heart.

Although the above embodiments describe the surgical procedure or method of the present invention as having a particular number and order of steps, the surgical procedure of the present invention is not limited to such steps or order of steps.

It is therefore an advantage of the present invention to provide surgical procedure which is minimally invasive.

Another advantage of the present invention is to provide a surgical procedure for implanting a blood pump in a patient's body which significantly reduces the time, costs and patient recovery time associated with such a procedure.

A further advantage of the present invention is to provide a surgical procedure for implanting a blood pump in a patient's body without the need for insertion of cardiopulmonary bypass, which further reduces time, additional costs, and patient recovery time associated with such a procedure.

Other objects, features and advantages of the invention will be apparent from the following detailed disclosure, taken in conjunction with the accompanying sheets of drawings, wherein like numerals refer to like parts, elements, components, steps and processes.

DETAILED DESCRIPTION

Figure 1:
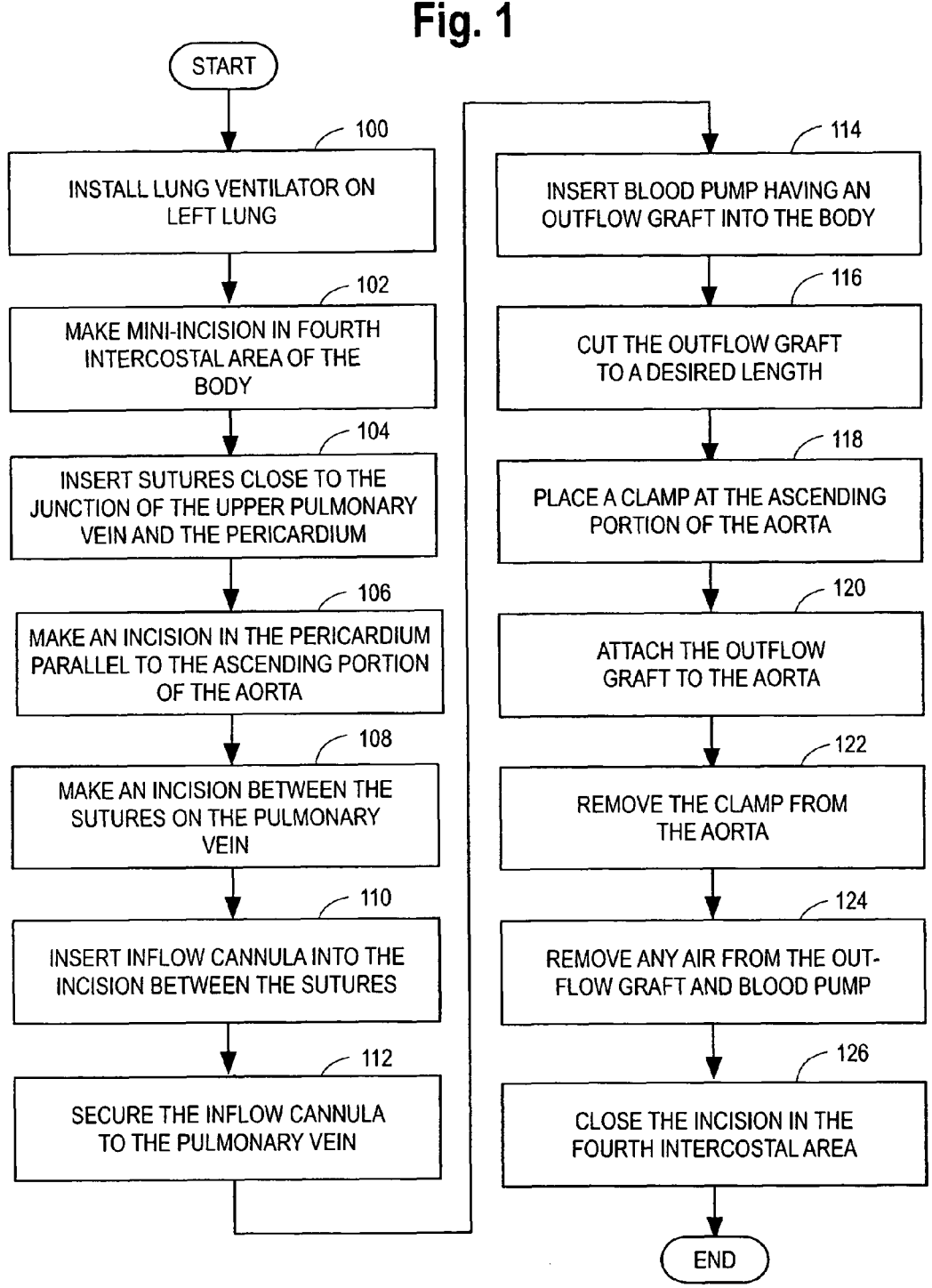
FIG. 1 is a schematic diagram illustrating one embodiment of the surgical implant procedure of the present invention.
Figure 2:
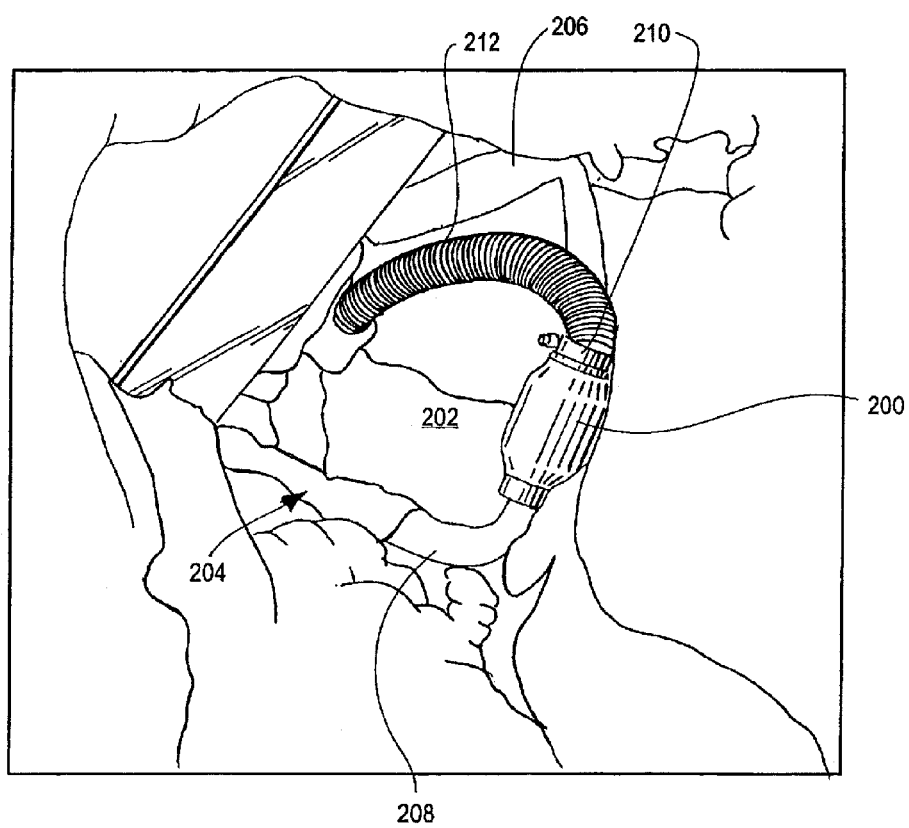
FIG. 2 is a perspective view of a heart pump attached to a heart of a patient according to the procedure of the present invention.

Referring to FIGS. 1 and 2, a surgical procedure or method for implanting blood pumps according to the present invention is illustrated where the surgical procedure is minimally invasive and significantly reduces the time, costs and patient recovery time associated with conventional blood pump implantation procedures.

Initially, a double lumen tracheal tube is inserted in a patient and connected to a respirator or lung ventilation device as shown by block 100 to assist the patient in the exchange of oxygen and carbon dioxide (sometimes referred to as artificial respiration) during the surgical procedure. In the surgical procedure of the present invention, a mini blood pump or LVAD 200 is connected to the left side of the heart 202 such as the blood pump disclosed by U.S. patent application Ser. No. 11/003,810, the subject matter of which is incorporated herein by reference. The blood pump or LVAD enhances the pumping of the blood through the body. The lung ventilator therefore is disconnected from the right lung which gives access to the insertion site inside the right thoracic cavity. The lung ventilator is connected via a single lumen tracheal tube to the lung delivering sufficient oxygenation during the surgical procedure. It should be appreciated that the lung ventilator may be any suitable ventilator or ventilation device.

After the lung ventilator is attached to the left lung of the patient and the right lung is deflated, a mini-incision or relatively small incision is made on the patient's body as described by block 102. More specifically, the mini-incision is made on the patient's chest area at the fourth intercostal space. The fourth intercostal space is the space between the fourth and fifth ribs of the patient on the right side of the patient's chest. The incision may be made at other suitable locations on the chest, however, such locations have been found to be less desirable. The fourth intercostal space enables the heart pump to be placed adjacent to the patient's diaphragm. The mini-incision or mini-thoracotomy is approximately three inches long. It should be appreciated that the size or length of the incision may be shorter. It should also be appreciated that any suitable size or type of incision may be made to access the heart and surrounding internal areas of the patient.

The incision allows access to the right thoracic cavity which includes the heart and the arteries and veins attached to the heart. As shown by block 104, the upper right pulmonary vein 204 is identified and concentric purse-string sutures are placed near or adjacent to the junction of the upper right pulmonary vein 204 and the pericardium 206.

The pulmonary veins return the arterialized blood from the lungs to the left atrium of the heart. There are four pulmonary veins, two from each lung. The pericardium 206 is the membranous sac that covers the heart and the base of the blood vessels that are attached to the heart. The purse-string sutures, which are the stitches surgeons use to hold skin, organs, blood vessels and all other tissues of the human body together, are placed on the upper right pulmonary vein near the junction of the pericardium and left untied. The sutures are inserted at this point to have them in place ready to be tied to save valuable time later in the procedure. It should be appreciated that any suitable number and type of sutures may be placed at the junction of the upper right pulmonary vein and pericardium.

After the sutures are in place, an incision is made in the pericardium parallel to the ascending aorta or the ascending portion of the aorta as shown by block 106. In making this incision, extreme care must be used to avoid damaging the right phrenic nerve of the patient. Another incision is made between the concentric purse-string sutures on the upper right pulmonary vein as shown by block 108. This incision can be any suitable type of incision having any suitable pattern. This incision will form the insertion and connection point for an inflow cannula to one side of the blood pump 200.

As shown by block 110, the blood flow inlet end of the inflow cannula 208, which is distal to the pump 200, is inserted into the upper right pulmonary vein 204 via the incision made in this vein. In one embodiment, at least one x-ray is directed at the patient's body and more specifically, at the patient's chest to provide a clearer picture or view of the inflow cannula on a display device such as a television monitor as the inflow cannula is being inserted in the upper right pulmonary vein. The x-rays thereby assist a surgeon in seeing, controlling and guiding the insertion of the inflow cannula in the patient's body. In this embodiment, the inflow cannula 208 is inserted through the mitral valve and into the left ventricular chamber of the heart. The mitral valve is a valve of the heart, composed of two triangular flaps, located between the left atrium and left ventricle of the heart which regulates blood flow between these chambers. Specifically, the mitral valve acts as a one-way valve that allows blood to pass from the left atrium into the left ventricle of the heart and normally prohibits blood flow in the opposite direction.

In one embodiment, the inflow cannula 208 is a substantially rigid tube which includes at least one and preferably a first and second sharp bend or curve and at least one other curve near a proximal end of the tube. The first sharp bend or curve is formed to allow the blood pump to sit on a patient's diaphragm while lining up an outflow graft, which is connected to the blood pump, to be inserted into the ascending portion of the aorta. The first bend or curve is optional depending on the actual configuration of the blood pump 200. The second sharp bend or curve enables the inflow cannula to be inserted through the left atrium through the mitral valve and into the left ventricle.

The inflow cannula 208 is a specially fabricated tube that is made in different sizes and has different bend or curvature radii based on different sizes of patients. The inflow cannula therefore can be custom manufactured to meet individual needs. In one embodiment, the size of the inflow cannula for a particular implant procedure is pre-determined or determined prior to surgery by using non-invasive diagnostic equipment such as a CT scan, which scans and displays an image of the inside of the patient's body. In this embodiment, the diameter of the inflow cannula is between 6 and 9 mm to allow therapeutic blood flows while not being too large to be detrimental to the blood flow through the upper right pulmonary vein. It should be appreciated that the diameter of the inflow cannula may be any suitable size or dimension. In one embodiment, the inflow cannula is made of titanium. In another embodiment, the inflow cannula is made with silicone or a reinforced silicone material. It should be appreciated that any suitable biocompatible material may be used that has the proper strength characteristics and ability to hold proper shape and structure.

In one embodiment, the inflow cannula 208 has two ends where at least one of the ends includes a removable balloon-tipped catheter or occluder. The catheter helps to prevent aspiration of air into the left atrium and left ventricle during the surgical implantation procedure.

Referring to FIG. 1, the inflow cannula is secured to the upper right pulmonary vein 204 as shown by block 112. In one embodiment, the sutures inserted near the junction of the upper right pulmonary vein 204 and the pericardium 206 are tightened or tied to secure the inflow cannula to the upper right pulmonary vein. Alternatively, the inflow cannula is secured in place by using a clamp (such as clamp 210) connected to the outside perimeter or surface of the inflow cannula and the upper right pulmonary vein. The clamp helps to prevent blood leakage and/or damage to the upper right pulmonary vein.

As shown by block 114 in FIG. 1, a blood pump such as a mini-blood pump 200 or other blood assist device is inserted into the patient's body. In this embodiment, the blood pump includes an outflow member or outflow tube or outflow graft 212. The outflow graft may be interconnected to the blood pump or attached separately as an independent component. The outflow graft 212 is similar to the inflow cannula 208 and may be any suitable tube or tubing. In one embodiment, the outflow graft is a cardiovascular graft or corrugated tube. It should be appreciated that the outflow graft may be any suitable tube and may have any suitable size and/or shape. The outflow graft is cut to a desired length based at least in part on the connection location of the open end of the outflow graft.

A specially shaped aortic tangential clamp is inserted through the opening in the patient's body and attached to the ascending portion of the aorta as shown by block 118. The clamp may be any suitable clamp or clamps and is secured to or attached to the aorta. The clamp reduces the bleeding from the aorta and helps to prevent damage to the aorta. As shown by block 120, the outflow graft 212 of the blood pump is attached to the aorta by using a suitable sewing procedure such as an end-to-side anastomosis, which is a surgical joining of two ducts such as blood vessels, to allow blood flow from one to the other. The anastomisis is a minimally invasive surgery technique using specially designed surgical tools.

When the outflow graft 212 is connected or attached to the aorta, the clamp attached to the aorta is removed to restore normal blood flow through the aorta as shown by block 122. The outflow graft and blood pump are then flushed or de-aired to remove any air remaining in the outflow graft and the blood pump as shown by block 124. In one embodiment, a small needle is inserted into the outflow graft and/or blood pump to withdraw or remove air from the outflow graft and blood pump. After the air is removed from the outflow graft and blood pump, the blood pump is connected to the inflow cannula and secured to the inflow cannula using a suitable clamp or other suitable connector.

The blood pump or LVAD 200 can now function to assist the patient in pumping blood through the heart and more specifically through the left side of the heart. The surgical procedure is completed by sealing or closing the mini-incision made in the fourth intercostal area as described by block 126. The minimally invasive procedure of the present invention described above reduces the time and costs associated with the surgical implantation procedure as well as the post-operative recovery time of patients.

In one alternative embodiment, an end cap is pre-attached or pre-connected to the inflow cannula. The end cap is removed when the inflow cannula is secured and then the blood pump is connected to the inflow cannula. In this embodiment, the end cap functions as an occluder to block the flow of veinous blood during installation of the cannula.

It should be appreciated that although the above embodiments or examples of the surgical procedure of the present invention may be performed in any suitable order and the surgical procedure is not limited to those steps described above.

While the present invention is described in connection with what is presently considered to be the most practical and preferred embodiments, it should be appreciated that the invention is not limited to the disclosed embodiments, and is intended to cover various modifications and equivalent arrangements included within the spirit and scope of the claims. Modifications and variations in the present invention may be made without departing from the novel aspects of the invention as defined in the claims, and this application is limited only by the scope of the claims.

The invention is claimed as follows:

1. A minimally invasive surgical method for long term implantation of a blood pump comprising:
   (a) making an initial incision in a chest of a patient's body, wherein the patient's body further comprises a pericardium, an upper right pulmonary vein, a junction of the pericardium and the upper right pulmonary vein, an aorta, a mitral-valve, a left ventricular chamber of the patient's heart, and a left lung;
   (b) inserting a plurality of sutures on the upper right pulmonary vein adjacent to the junction of the pericardium and the upper right pulmonary vein;
   (c) making an incision in the pericardium substantially parallel to an ascending portion of the aorta;
   (d) making an incision between said sutures on the upper right pulmonary vein;
   (e) inserting an inflow cannula into the upper right pulmonary vein through the mitral-valve and into the left ventricular chamber;
   (f) securing the inflow cannula to the upper right pulmonary vein;
   (g) inserting a blood pump having an outflow graft in the patient's body;
   (h) attaching the outflow graft to the aorta;
   (i) connecting the blood pump to the inflow cannula, wherein the blood pump remains in the patient after the initial incision is closed and the blood pump assists in pumping blood through the patient's heart.

2. The surgical method of claim 1, further comprising attaching a lung ventilator to the patient's left lung.

3. The surgical method of claim 1, wherein the initial incision is made in the fourth intercostal space on the right side of the patient's body.

4. The surgical method of claim 3, wherein making the initial incision in the patient's body in the fourth intercostal space includes performing a thoracotomy.

5. The surgical method of claim 1, further comprising cutting the outflow graft to a desired length.

6. The surgical method of claim 1, further comprising attaching a tangential clamp to the aorta prior to attaching the outflow graft to the aorta.

7. The surgical method of claim 6, further comprising removing the tangential clamp after the outflow graft is attached to the aorta.

8. The surgical method of claim 1, further comprising removing air from at least the outflow graft and the blood pump after the outflow graft is attached to the aorta.

9. The surgical method of claim 1, wherein the length of at least the initial incision is less than or equal to three inches.

10. The surgical method of claim 1, wherein making the incision between said sutures on the upper right pulmonary vein includes making a cross-wise incision.

11. The surgical method of claim 1, wherein inserting the inflow cannula into the upper right pulmonary vein includes inserting a substantially rigid tube having a distal end and a proximal end, at least one bend and a curvature adjacent to the proximal end.

12. The surgical method of claim 1, wherein a diameter of the inflow cannula is between 6 and 9 mm.

13. The surgical method of claim 1, wherein the inflow cannula is made of at least one of the materials selected from the group consisting of: titanium and silicone.

14. The surgical method of claim 1, wherein at least one end of the inflow cannula includes a removable balloon-tipped catheter.

15. The surgical method of claim 1, further comprising directing at least one X-ray at the patient's body and viewing at least one picture on a display device based on said X-ray.

16. The surgical method of claim 1, wherein securing the inflow cannula to the upper right pulmonary vein includes tightening said sutures.

17. The surgical method of claim 1, wherein securing the inflow cannula to the upper right pulmonary vein includes attaching a clamp to the end of the inflow cannula positioned adjacent to the upper right pulmonary vein and securing the clamp to the upper right pulmonary vein.

18. The surgical method of claim 1, wherein the outflow graft includes a cardiovascular graft.

19. The surgical method of claim 1, wherein attaching the outflow graft to the aorta includes sewing the outflow graft to the aorta.

20. The surgical method of claim 1, wherein attaching the outflow graft to the ascending aorta includes performing an end-to-side anastomosis.

21. A minimally invasive surgical method for implanting a blood pump comprising:
   (a) accessing at least a patient's pericardium, upper right pulmonary vein, a junction of the pericardium and the upper right pulmonary vein, an aorta, a mitral-valve, a left ventricular chamber of the patient's heart, and a left lung through an initial incision in a patient's chest;
   (b) inserting a plurality of sutures on the upper right pulmonary vein adjacent to the junction of the pericardium and the upper right pulmonary vein;
   (c) making an incision in the pericardium substantially parallel to the ascending portion of the aorta;
   (d) making an incision between said sutures on the upper right pulmonary vein;
   (e) connecting a blood pump to a rigid inflow cannula, wherein said blood pump includes at least one end cap and assists blood flow through the heart;
   (f) implanting the blood pump and inflow cannula into the patient's body and further inserting the rigid inflow cannula into the upper right pulmonary vein;
   (g) securing the rigid inflow cannula to the upper right pulmonary vein, wherein the rigid inflow cannula and blood pump remains in the patient after the surgical method is completed;
   (h) inserting and attaching an outflow graft to the aorta; and
   (i) closing the initial incision, wherein at least the rigid inflow cannula and blood pump remains in the patient after the initial incision is closed.

22. The surgical method of claim 21, further comprising attaching a lung ventilator to the patient's left lung.

23. The surgical method of claim 21, wherein the initial incision is made on the right side of the patient's body.

24. The surgical method of claim 21, wherein making the initial incision includes performing a thoracotomy.

25. The surgical method of claim 21, wherein the inflow cannula is inserted into the upper right pulmonary vein, through the mitral-valve and into the left ventricular chamber.

26. The surgical method of claim 25, wherein inserting the inflow cannula into the upper right pulmonary vein, through the mitral-valve and into the left ventricular chamber includes inserting a substantially rigid tube having a distal end and a proximal end, at least one bend and a curvature adjacent to the proximal end.

27. The surgical method of claim 21, further comprising cutting the outflow graft to a desired length.

28. The surgical method of claim 21, further comprising attaching a tangential clamp to the ascending aorta prior to attaching the outflow graft to the aorta.

29. The surgical method of claim 28, further comprising removing the clamp after the outflow graft is attached to the aorta.

30. The surgical method of claim 21, further comprising removing air from at least the outflow graft and the blood pump after the outflow graft is attached to the aorta.

31. The surgical method of claim 21, wherein the length of at least the initial incision is less than or equal to three inches.

32. The surgical method of claim 21, wherein at least one end of the inflow cannula includes a removable balloon-tipped catheter.

33. The surgical method of claim 21, further comprising directing at least one X-ray at the patient's body and viewing at least one picture on a display device based on said X-ray.

34. The surgical method of claim 21, wherein securing the inflow cannula to the upper right pulmonary vein includes tightening said sutures.

35. The surgical method of claim 21, wherein securing the inflow cannula to the upper right pulmonary vein includes attaching a clamp to the end of the inflow cannula positioned adjacent to the upper right pulmonary vein and securing the clamp to the upper right pulmonary vein.

36. The surgical method of claim 21, wherein the outflow graft includes a cardiovascular graft.

37. The surgical method of claim 21, wherein attaching the outflow graft to the aorta includes sewing the outflow graft to the aorta.

38. The surgical method of claim 21, wherein attaching the outflow graft to the aorta includes performing an end-to-side anastomosis.

39. The surgical method of claim 21, wherein the rigid inflow catheter contains at least one bend.

40. The surgical method of claim 39, wherein the rigid inflow catheter contains a second bend.

41. The surgical method of claim 40, wherein the rigid inflow catheter contains a curve near its proximal end.

42. The surgical method of claim 39, wherein the at least one bend comprises curvature radii based on different sizes of patients.

43. The surgical method of claim 39, wherein the at least one bend facilitates positioning of the blood pump on the patient's diaphragm.

44. The surgical method of claim 40, wherein the second bend allows the inflow cannula to be inserted through the left atrium, through the mitral valve, and into the left ventricle.

* * * * *